United States Patent [19]

Schroeder et al.

[11] 4,097,530

[45] Jun. 27, 1978

[54] PROCESS FOR THE PRODUCTION OF SQUARIC ACID

[75] Inventors: Manfred Schroeder; Wolfgang Schaefer, both of Marl, Germany

[73] Assignee: Chemische Werke Huels Aktiengesellschaft, Marl, Germany

[21] Appl. No.: 798,546

[22] Filed: May 19, 1977

[30] Foreign Application Priority Data

May 28, 1976   Germany ............................ 2623836

[51] Int. Cl.$^2$ ............................................. C07C 45/00
[52] U.S. Cl. .............................. 260/586 P; 260/586 R
[58] Field of Search ......................... 260/586 R, 586 P

[56] References Cited

U.S. PATENT DOCUMENTS 3,833,489   9/1975   Ercoli et al. ..................... 260/586 R

FOREIGN PATENT DOCUMENTS 1,568,291   3/1970   Germany.

OTHER PUBLICATIONS

West et al., "JACS", 85:2584 (1963).
Solomon et al., "J. Org. Chem.", 37:1551 (1966).
West et al., "J.A.C.S.", 81:3480 (1959).
Semmelhack et al., "Tetra Letters", No. 16, 1061-4 (1971).
Maahs, "Liebigs Ann. Chem.", 686,55 (1965).
Maahs et al., "Angew. Chim.", 75:982 (1963).

Primary Examiner—Norman Morganstern
Attorney, Agent, or Firm—Millen & White

[57] ABSTRACT

A process for the production of squaric acid, comprising reacting hexachlorocyclobutene with 70-96% by weight sulfuric acid at 80°-150° C.

7 Claims, No Drawings

PROCESS FOR THE PRODUCTION OF SQUARIC ACID

BACKGROUND OF THE INVENTION

This invention relates to an improved process for the preparation of squaric acid (1,2-dihydroxy-3,4-cyclobutenedione).

A number of methods for the production of quadratic acid have been proposed. In accordance with J. Amer. Chem. Soc. 81 : 3480 (1959), squaric acid is produced in a yield of 56% by cyclically dimerizing monochlorotrifluoroethylene and thereafter dechlorinating the product to the perfluorocyclobutene. The latter is reacted with an alcoholate to form the 1,2-dialkoxytetrafluorocyclobutene, the squaric acid then being produced by hydrolyzing the last-mentioned reaction product.

According to another process known from "Angew. Chemie" [Applied Chemistry] 75 : 982 (1963), as well as from "Liebigs Ann. Chem." [Liebig's Annals of Chemistry] 686 : 55 (1965), hexachlorobutadiene is first reacted with an elthylate to form 1-ethoxypentachlorobutadiene-(1,3). The latter is cyclized to the perchlorocyclobutenone, and squaric acid is produced therefrom by hydrolysis. The total yield in this case is 40%.

In a further process according to J. Amer. Chem. Soc. 85 : 2584 (1963), squaric acid can be obtained in a yield of 60% from 1,2-dichlorotetrafluorocyclobutene-(1) by hydrolyzing 2-chloro-3,3-difluoro-2,4,4-trimethoxycyclobutene.

In a still further process according to DOS [German Unexamined Laid-Open Application] 1,568,291, squaric acid can be obtained in a 40% yield from hexachlorobutadiene and morpholine by way of the intermediate stages of trichlorotrimorpholinobutadiene and $\beta$-morpholinotrichlorocyclobutenone.

All of these processes are very costly due to the large number of process stages and are also unsatisfactory from the standpoint of the thus-obtained yields. In addition, numerous undesirable and useless by-products are formed which, in most cases, require an isolation of the intermediate products before the further processing thereof.

SUMMARY OF THE INVENTION

A principal object of this invention is to provide an improved process for the production of squaric acid.

Upon further study of the specification and appended claims, further objects and advantages of this invention will become apparent to those skilled in the art.

These objects are attained by heating hexachlorocyclobutene with 70–96% sulfuric acid to temperatures of between 80° and 150° C.

The amount of the acid is suitably proportioned so that the amount of water required for the hydrolysis can be removed from the sulfuric acid without allowing the sulfuric acid concentration, which increases during the reaction, to rise substantially above 96%, i.e. not higher than 98%, preferably not more than 95%. To maintain the concentration of sulfuric acid at the desired level, it is also possible to add water continuously during the reaction. In this way, the sulfuric acid concentration can be maintained at a constant value during the course of the reaction. It is possible to use a large excess of sulfuric acid.

Normally, an approximately 1- to 10-fold quantity by weight of acid, based on hexachlorocyclobutene, is sufficient as the reaction medium. The required water can be introduced into the reaction as such or in the form of a diluted sulfuric acid. An approximately 2- to 5-fold amount by weight of the acid has proven to be especially advantageous.

The reaction is conducted with 70–96% by weight aqueous sulfuric acid. With a more concentrated acid, the hydrolysis reaction is very weak owing to the low amount of water present; in case of a concentration lower than 70%, the cleavage tendency of the chloride anion from the hexachlorocyclobutene is reduced to such an extent that, even with the use of higher temperatures and pressures, only minor amounts of quadratic acid can be formed. A sulfuric acid with a concentration of about 85 to 95%, especially about 90% is preferred, since such a concentration contains sufficient water favorable for the hydrolysis, and results in a high reaction velocity.

The reaction is generally conducted at temperatures of between 80° and 150° C. under ambient pressure. Below 80° C., the reaction velocity is undesirably low, At above 150° C., carbonization reactions occur with losses of yield. Additionally, at such high temperatures, the rearrangement of the hexachlorocyclobutene to the straight-chain isomer hexachlorobutadiene is initiated, the latter compound being unreactive in the reaction medium.

It is preferred for the reaction to be conducted at 100°–140° C. because in that range the reaction velocity is high and the formation of by-products is very low. A temperature of about 110° to 130° C., especially 120° C. proved to be particularly suitable. To obtain a quick an complete reaction the heterogeneous mixture of sulfuric acid and hexachlorocyclobutene has to be stirred vigorously thereby obtaining a dispersion of finely divided droplets of the hexachlorocyclobutene in the acid reaction medium in order to presend sufficient surface for the reaction. With slow stirring the reaction also is slow.

When the reaction is conducted, squaric acid begins to precipitate from the hot acid after a short period of time, e.g., about 15 to 30 minutes, under the evolution of hydrogen chloride. Within a few hours, normally 4–8 hours, the reaction is completed. Upon cooling to room temperature, practically the entire amount of squaric acid is crystallized out. The yield of pure squaric acid after filtration, repeated washing with ice water, and drying, is more than 93%.

The hexachlorocyclobutene used as the starting compound can be prepared from hexafluorocyclobutene or 1,2-dichlorotetrafluorocyclobutene (J. Org. Chem. 31 : 1551–1553 [1966] and Tetrahedron Letters 16 : 1061 [1971]).

A fraction rich in hexachlorocyclobutene can also be produced from hexachlorobutadiene formed as a by-product during the manufacture of perchlorinated hydrocarbons ("Angew. Chem." 78 : 927–929 [1966]). A special advantage of this invention is that it is possible to utilize such mixtures of hexachlorocyclobutene and hexachlorobutadiene in the process of this invention, since it is unnecessary to conduct an expensive fine purification of the hexachlorocyclobutene. If such mixtures are employed, the hexachlorobutadiene, which is stable with respect to the acid, remains in the pure form and can be separated from the reaction mixture as a liquid organic phase. (Such mixtures usually comprise about 2 to 50 parts by weight of the hexachlorobutadiene per part by weight of hexachlorocyclobutene.)

Squaric acid is known to be a valuable intermediate for the production of stabilizers, dyes, bactericides, and fungicides, an example of how to use this acid being found in DOSS [German Unexamined Laid-Open Applications] 2,055,894 and 2,616,756.

By means of the process according to the present invention, it is now possible for the first time to find a simple and rapidly occurring reaction, leading to a readily isolatable, pure squaric acid without any substantial formation of by-products and with practically quantitative rates of conversion and an almost quantitative yield.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A mixture of 30 g. (0.114 mol) of hexachlorocyclobutene (purity 99.2%), having a melting point of +50° C., and 90 ml. (163 g.) of 90% sulfuric acid is heated under vigorous agitation to 120° C. After a short period of time, a uniform hydrogen chloride stream evolves which slows down abruptly after 5 hours. To remove the residual gaseous hydrogen chloride more quickly, a small amount of nitrogen is introduced into the reaction mixture, and the latter is further agitated at 120° C. for 3 hours. During the reaction, the hexachlorocyclobutene, which is sparingly soluble in the sulfuric acid and is liquid at the reaction temperature, gradually disappears, while crystalline squaric acid simultaneously begins to separate. After termination of the reaction, the mixture is cooled to room temperature, allowed to stand overnight to complete the settling of the crystals, and thereafter is vacuum-filtered through a porous glass plate. The crystalline slurry is washed three times with 10 ml. portions of ice water and dried. Yield: 12.1 g. (0.106 mol) of squaric acid, 93% of theory. Acid number: 982.1 (theoretical 983.3).

EXAMPLE 2

A mixture of 4.0 kg. of 95% hexachlorocyclobutene (impurity: hexachlorobutadiene) (14.57 mol) and 12 l. (21.7 kg) of 90% sulfuric acid is heated under vigorous agitation for 10 hours to 120° C. The thus-produced gaseous hydrogen chloride is absorbed in a scrubbing tower connected downstream thereof. Toward the end of the reaction, a small amount of nitrogen is introduced into the reaction mixture to purge the residual hydrogen chloride. Thereafter, the mixture is cooled to room temperature and allowed to stand for 12 hours. The thus-separated squaric acid crystals are vacuum-filtered, and to remove the adhering hexachlorobutadiene, washed with 1.5 l. of hexane and then, to remove the sulfuric acid, washed three times with reapectively one-liter portion of ice water. After drying, 1,442 g. of squaric acid (12.64 mol) is obtained, acid number: 982.9.

From the wash water, after neutralization with sodium hydroxide solution and after adding aqueous $CuSO_4$ solution, there is recovered under heating 52 g. (0.3 mol) of the copper salt of squaric acid. Total yield: 88.8% of theory.

The sulfuric acid removed by the vacuum-filtration step is washed with 3 l. of hexane. The combined hexane solutions result in 134 g. of hexachlorobutadiene after evaporation under vacuum.

EXAMPLE 3

A mixture of 4 kg. of 98% hexachlorocyclobutene (15 mol) and 8 l. (14.5 kg.) of 90% sulfuric acid is heated under vigorous agitation to 115° C. As soon as the reaction temperature is reached, 760 g. of water in the form of 950 g. of 20% sulfuric acid is continuously and uniformly added to the reaction mixture within a period of 6 hours. The hydrogen chloride gas, produced in large amounts, is absorbed in a suitable scrubbing tower. After the dilute sulfuric acid has been added in its entirety, the mixture is heated for 4 hours to 120° C. and then a mild stream of nitrogen stream is introduced into the reaction mixture, and the latter is thereafter allowed to cool. To separate the squaric acid crystals entirely, the mixture is allowed to stand overnight, then subjected to a thorough vacuum-filtration step. The colorless crystalline slurry is first washed three times with respectively 0.5 l. of hexane and then three times with respecively 1 l. of ice water. After drying, 1,488 g. (13 mol) of squaric acid is obtained. Yield: 86.7% of theory.

In the wash water, 0.7 mol of squaric acid can be detected.

EXAMPLE 4

60 g. of a mixture of 50% by weight of hexachlorocyclobutene and 50% by weight of hexachlorobutadiene (0.114 mol of hexachlorocyclobutene) is heated together with 80 ml. of 86% sulfuric acid under vigorous agitation of 125° C. After 8 hours, the evolution of hydrogen chloride decreases sharply. The mixture is maintained at this temperature for another 7 hours, then cooled to room temperature, and combined with 100 ml. of hexane under agitation. After allowing the mixture to stand overnight, the thus-separated crystals are vacuum-filtered and then washed first with a small amount of hexane and then three times with a small amount of water. After drying under vacuum, 9.7 g. of squaric acid (0.085 mol) is obtained. Yield: 74.6%.

The combined hexane solutions yield 28.5 g. of hexachlorobutadiene after removal of the solvent under vacuum.

EXAMPLE 5

30 g. (0.114 mol) of hexachlorocyclobutene (purity 99%) and 33 ml. of 90% sulfuric acid (60 g.) are heated under vigorous agitation to 120° C. Within one hour, 10 ml. of water is added dropwise to the reaction mixture. After a short period of time, and with the evolution of hydrogen chloride, the organic phase gradually disappears and squaric acid beings to precipitate.

After all of the water has been added, the mixture is heated for another 3 hours to 120° C., allowed to cool down overnight under agitation, and then is thoroughly vacuum-filtered through a porous glass plate. The crystals are washed twice with hexane and then three times with 10 ml. portions of ice water. Yield: 11.9 g. (0.104 mol), 91.5% of theory.

EXAMPLE 6

10 g. (37.6 millimoles) of hexachlorocyclobutene (purity 98%) and 30 ml. of 90% sulfuric acid are heated under vigorous agitation to 85° C. The thus-produced hydrogen chloride (about 10 millimoles of HCl per hour) is collected in 1N sodium hydroxide solution. After 17 hours, the reaction mixture is worked up as indicated in the previous examples. Yield: 2.7 g. of squaric acid (63% of theory).

EXAMPLE 7

30 g. (0.114 mol) of hexachlorocyclobutene (purity 98%) and 90 ml. of 90% sulfuric acid are heated under vigorous agitation to 140° C. The evolution of hydrogen chloride markedly decreases after 2 hours. By the introduction of nitrogen, the residual hydrogen chloride gas is purged during the course of 3 hours. The mixture is worked up as described in Example 1. The thus-obtained squaric acid has a slighthly grey color due to carbonization products. By dissolution in hot water, filtration, and subsequent cooling, an analytically pure product can be isolated.

Yield: 8.9 g. of squaric acid (0.078 mol); 68.4% of theory.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of squaric acid, comprising reacting hexachlorocyclobutene with 70-96% by weight sulfuric acid at 80°-150° C.

2. A process according to claim 1, wherein the reaction mixture is heated to a temperature of 100°-140° C.

3. A process according to claim 1, wherein the reaction mixture is heated to a temperature of about 120° C.

4. A process according to claim 1, wherein the sulfuric acid is 90% by weight.

5. A process according to claim 1, wherein the weight ratio of hexachlorocyclobutene to acid is 1 : 1 to 1 : 10, respectively.

6. A process according to claim 1, wherein the weight ratio of hexachlorocyclobutene to acid is 1 : 2 to 1 : 5, respectively.

7. A process according to claim 1, wherein the hexachlorocyclobutene is in a mixture with hexachlorobutadiene.

* * * * *